United States Patent
Flores-Candia et al.

(10) Patent No.: US 9,254,252 B2
(45) Date of Patent: Feb. 9, 2016

(54) COMPOUNDS

(71) Applicant: DSM IP ASSETS B.V., Heerlen (NL)

(72) Inventors: Juana Lucia Flores-Candia, Basel (CH); Karina Hecker, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/347,401

(22) PCT Filed: Sep. 24, 2012

(86) PCT No.: PCT/EP2012/068746
§ 371 (c)(1),
(2) Date: Mar. 26, 2014

(87) PCT Pub. No.: WO2013/045383
PCT Pub. Date: Apr. 4, 2013

(65) Prior Publication Data
US 2014/0371328 A1      Dec. 18, 2014

(30) Foreign Application Priority Data

Sep. 26, 2011 (EP) ..................................... 11182706

(51) Int. Cl.
| | | |
|---|---|---|
| *A61K 8/55* | (2006.01) | |
| *A61K 8/34* | (2006.01) | |
| *A61K 8/37* | (2006.01) | |
| *A61Q 19/00* | (2006.01) | |
| *A61K 8/02* | (2006.01) | |
| *A61K 8/06* | (2006.01) | |
| *A61Q 19/02* | (2006.01) | |

(52) U.S. Cl.
CPC ................ *A61K 8/556* (2013.01); *A61K 8/0295* (2013.01); *A61K 8/062* (2013.01); *A61K 8/342* (2013.01); *A61K 8/347* (2013.01); *A61K 8/37* (2013.01); *A61K 8/375* (2013.01); *A61Q 19/02* (2013.01); *A61K 2800/52* (2013.01)

(58) Field of Classification Search
CPC ......... A61K 8/347; A61K 8/37; A61K 8/375; A61K 8/556; A61K 8/0295; A61K 8/062; A61K 8/342; A61K 2800/52; A61Q 19/002; A61Q 19/00; A61Q 19/08; A61Q 19/10; A61Q 17/04; A61Q 1/02
USPC ........................... 424/401; 514/733; 558/186
See application file for complete search history.

(56) References Cited

U.S. PATENT DOCUMENTS

| | | | |
|---|---|---|---|
| 6,124,364 A | 9/2000 | Breton et al. | |
| 6,414,037 B1 | 7/2002 | Pezzuto et al. | |
| 2002/0173472 A1 | 11/2002 | Pezzuto et al. | |
| 2002/0183400 A1 | 12/2002 | Baldo et al. | |
| 2004/0175347 A1 | 9/2004 | Bissett | |
| 2006/0204526 A1 | 9/2006 | Lathrop et al. | |
| 2006/0269494 A1* | 11/2006 | Gupta | 424/70.1 |
| 2010/0173027 A1 | 7/2010 | Kroepke et al. | |
| 2010/0310615 A1 | 12/2010 | Vercauteren | |

FOREIGN PATENT DOCUMENTS

| | | |
|---|---|---|
| DE | 10 2006 027138 | 12/2007 |
| EP | 1 234 571 | 8/2002 |
| FR | 2 777 183 | 10/1999 |
| FR | 2 923 717 | 5/2009 |
| WO | WO 01/30336 | 5/2001 |

OTHER PUBLICATIONS

International Search Report for PCT/EP2012/068746 mailed Oct. 25, 2012.

\* cited by examiner

*Primary Examiner* — Blessing M Fubara
(74) *Attorney, Agent, or Firm* — Nixon & Vandernye P.C.

(57) ABSTRACT

The present invention relates to topical compositions comprising resveratrol in a liquid crystal gel network formed by a phosphate ester surfactant and a co-emulsifier. The present invention also relates to the process to make such compositions.

15 Claims, No Drawings

COMPOUNDS

This application is the U.S. national phase of International Application No. PCT/EP2012/068746 filed 24 Sept. 2012 which designated the U.S. and claims priority to EP 11182706.9 filed 26 Sept. 2011, the entire contents of each of which are hereby incorporated by reference.

The present invention relates to topical compositions comprising resveratrol in a liquid crystal gel network formed by a phosphate ester surfactant and a solid co-emulsifier. The present invention also relates to the process to make such compositions.

Skin Care market is evolving toward cosmetic compositions with enhanced skin whitening properties as consumers are expressing strong interest in achieving uniform and lighter skin tone. Solar lentigos, post-inflammatory hyperpigmentation and melasma are skin disorder widely distributed in human population. Furthermore, the skin lightening market is one of the cosmetic market segments showing the biggest growth; driven largely by expanding Asian markets, as well as by extension of skin whitening products to specific consumer segments (i.e., men care). Different products exhibiting skin whitening activities exist in the market (e.g. Ascorbyl glucoside, arbutins, plant extracts, kojic acid, Vitamin C derivatives), however these often show formulation or penetration constraints, have low in-vivo efficacy and/or give rise to safety concerns. As consumers are becoming increasingly aware of the toxicity issues related to some of these whitening agents, there is an ongoing need for effective and safe whitening actives considered as "natural" and without major side effects.

Resveratrol, also referred to as 3,4',5-trihydroxystilbene, is a naturally occurring molecule found in red grapes and hence red wine, peanuts, knotweed, raspberries, blueberries, and certain other plant berries. This compound has been the subject of intense research in recent years. Scientific reports are increasingly demonstrating the multi-functional benefits of resveratrol. Resveratrol is reported to be an extremely potent anti-oxidant, a modulator of genetic expression via signal transduction, an inhibitor of inflammatory mediators, to have phytohormonal benefits, and to reduce the synthesis of melanine. Such combination of biological functions and the cosmetic effects makes resveratrol a unique active ingredient for personal care products.

Despite all the above biological properties and its superior skin whitening effects, the formulation of resveratrol into cosmetic compositions poses a set of challenges. One problem with resveratrol is that it is generally unstable in cosmetic compositions (such as O/W or W/O emulsions) as it induces phase separation in emulsions and promotes colour change from white to yellowish-brown. Accordingly, so far its use in cosmetic formulations is restricted to very small amounts. Furthermore, resveratrol tends to precipitate (crystallize) in cosmetic compositions containing water.

For the above outlined reasons the incorporation of high content resveratrol is believed only to be feasible in substantially water-free cosmetic compositions. Furthermore, different non-aqueous polar organic solvents such as PEG-solvents have been used to solubilize resveratrol before adding into O/W or W/O emulsions. However the amounts of solvents reported are extremely high. (See e.g. US 2007/0225360, EP123457, US 2002/0173472). Such high levels of solvents however may cause skin irritation if applied on damaged or sensitive skin. Moreover, high solvents levels are known to diminish the aesthetics in tactile properties such as skin feeling.

Thus, there is an ongoing need to overcome the drawbacks of the prior art and to find an acceptable solubilizer for resveratrol as well as a robust and stable emulsion system. Furthermore, the total solvent content of the cosmetic formulations should be low in order to diminish any adverse skin feel resulting thereof.

Surprisingly it has been found that resveratrol can be solubilised in a liquid crystal gel network formed by a phosphate ester surfactant such as by trilaureth-4 phosphate and a solid co-surfactant allowing e.g. the formulation of cosmetic emulsions free of solvents. Furthermore, topical compositions containing the solubilised resveratrol in a liquid crystal gel network exhibit good sensory properties as well as long term storage stability.

Thus, in a first embodiment the invention relates to topical compositions comprising resveratrol characterized in that the resveratrol is incorporated into a liquid crystal gel network formed by a phosphate ester surfactant and a co-emulsifier.

In another particular embodiment, the invention relates to a process for the preparation of a topical composition comprising an aqueous phase and an oily phase characterized in that the composition comprises resveratrol incorporated into a liquid crystal gel network formed by a phosphate ester surfactant and a solid co-emulsifier, said process comprising the steps of a.) Dissolving resveratrol in a phosphate ester surfactant by applying heat followed by
b1.) Adding the resveratrol/surfactant solution to the heated oily phase comprising the solid co-emulsifier followed by addition of the heated aqueous phase or
b2.) Adding the resveratrol/surfactant solution to the heated aqueous phase followed by the addition of the resulting mixture to the heated oily phase comprising the solid co-emulsifier followed by
c.) Homogenizing the resulting mixture.

Preferably, the dissolution in step a) is preformed at 30-60° C., most preferably at 35-50° C. The oily phase is preferably heated to a temperature selected in the range of 30-100° C., more preferably in the range of 50-90° C., most preferably in the range of 60-80° C. The aqueous phase is preferably heated to a temperature selected in the range of 25-60° C., more preferably in the range of 30-50° C., most preferably in the range of 35-45° C. After homogenizing the resulting composition is cooled down to ambient temperature (~20° C.) whereby the liquid crystal network is formed.

Resveratrol [CAS501-36-0, CA Name: 5-[(1E)-2-(4-hydroxyphenyl)ethenyl]-1,3-Benzenediol] is e.g. commercially available at DSM Nutritional Products Ltd.

Resveratrol is generally present in the topical compositions according to the invention in proportions ranging from 0.01 to 2 wt.-%, preferably from 0.05 to 0.5 wt.-%, most preferably about 0.1 to 0.3 wt.-% based on the total weight of the composition.

Phosphate esters surfactants suitable for incorporation into the compositions of the present invention have the formula

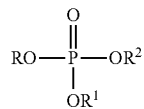

The phosphate ester surfactant has the general structure wherein R, $R^1$ and $R^2$ may be hydrogen, an alkyl of from 1 to about 22 carbons, preferably from about 12 to 18 carbons, or an alkoxylated alkyl of from 1 to about 22 carbons, preferably from about 12 to 18 carbons, and having 1 or more, preferably from about 2 to about 25, most preferably 2 to 12, moles ethylene oxide, with the provision that at least one of R, $R^1$ and $R^2$ is an alkyl or alkoxylated alkyl as previously defined but having at least 6 alkyl carbons in said alkyl or alkoxylated alkyl group.

Monoesters in which $R^1$ and $R^2$ are hydrogen and R is selected from alkyls of 10 to 18 carbons and alkoxylated fatty alcohols of 10 to 18 carbons and 2 to 12 moles ethylene oxide are preferred. Among the preferred phosphate ester surfactants, mention may be made of, C8-10 Alkyl Ethyl Phosphate, C9-15 Alkyl Phosphate, Ceteareth-2 Phosphate, Ceteareth-5 Phosphate, Ceteth-8 Phosphate, Ceteth-10 Phosphate, Cetyl Phosphate, C6-10 Pareth-4 Phosphate, C12-15 Pareth-2 Phosphate, C12-15 Pareth-3 Phosphate, DEA-Ceteareth-2 Phosphate, DEA-Cetyl Phosphate, DEA-Oleth-3 Phosphate, Potassium cetyl phosphate, Deceth-4 Phosphate, Deceth-6 Phosphate and Trilaureth-4 Phosphate.

Preferred phosphate ester surfactants according to the present invention are phosphate ester surfactants which are liquid at ambient temperature (20° C.). Particular suitable liquid phosphate ester surfactants are trilaureth-4 phosphate (e.g. available as Hostaphat KL 340D or SILAPHOS® TE 340), C8-C10 Phosphate (e.g. available as Crodafos™ 810A), PPG-5-Ceteth-10 Phosphate (e.g. available as Crodafos™ C10/5A), Cetoleth-5 Phosphate (e.g. available as Crodafos™ CO5A), Deceth-4 Phosphate (e.g. available as Crodafos™ D4A), Glycereth-26 Phosphate (e.g. available as Crodafos™ G26A), Oleth-5 Phosphate and Dioleyl Phosphate (e.g. available as Crodafos™ HCE), Potassium C12-12 Alkyl Phosphate (e.g. available as Crodafos™ 1213K), TEA C12-13 Alkyl Phosphate (e.g. available as Crodafos™ 1213T), C9-15 Alkyl Phosphate (e.g. available as Crodafos™ M915A), Oleth-10 Phosphate (e.g. available as Crodafos™ 010A), DEA Oleth-10 Phosphate (e.g. available as Crodafos™ 010D), Oleth-3 Phosphate (e.g. available as Crodafos™ 03A), DEA Oleth-3 Phosphate (e.g. available as Crodafos™ 03D), Trideceth-10 Phosphate (e.g. available as Crodafos™ T10A), Trideceth-5 Phosphate (e.g. available as Crodafos™ T5A) or Trideceth-6 Phosphate (e.g. available as Crodafos™ T6A). The most preferred phosphate ester surfactant according to the invention is trilaureth-4 phosphate [CAS 31800-90-5].

The phosphate ester surfactant is advantageously present in the topical compositions according to the invention in proportions ranging from 0.1 to 5 wt.-%, preferably from 0.5 to 5 wt.-%, most preferably from 1 to 3 wt.-% based on the total weight of the composition.

The ratio (w/w) of phosphate ester surfactant such as preferably trilaureth-4 phosphate to resveratrol is advantageously selected in the range of 200:1 to 5:1, preferably in the range of 50:1 to 9:1 such as in the range of 20:1 to 9:1 and particularly in the range of about 10:1.

In a particular advantageous embodiment, a liquid phosphate ester surfactant is used and resveratrol, prior to its incorporation into the composition, is dissolved in the liquid phosphate ester surfactant, preferably at its maximum dissolution level which might depend on the selected phosphate ester surfactant but can easily be established by a person skilled in the art.

The term "solid co-emulsifiers" refers to emulsifiers which are solid at ambient temperature (~20° C.). Particular suitable solid co-emulsifiers for the purpose of the present invention have a HLB-value<5 (with the proviso that the HLB is calculated according to Griffin by the following formula HLB=20*($M_h$/M), where $M_h$ is the molecular mass of the hydrophilic portion of the Molecule, and M is the molecular mass of the whole molecule, giving a result on an arbitrary scale of 0 to 20).

Preferred co-emulsifiers are selected from the group consisting of solid fatty acids (HLB 2.6-2.9) such as in particular palmitin-, stearin- or behenacid, solid fatty alcohols (HLB 1.0-1.6) such as in particular glycerol monostearate or $C_{12-22}$ alcohols, solid glycerin esters (HLB 3.2-4.5) such as in particular glyceryl monostearate, solid sorbitan esters (HLB 2.1-4.7) such as e.g. sorbitan stearate, solid polyglycerin esters (HLB 2.0-5.0) or methylglucoside esters (HLB 3.0-5.0) as well as mixtures thereof.

Particular preferred co-emulsifiers according to the present invention are non-ionic solid fatty alcohols having from 12 to 22 carbon atoms as well as mixtures thereof such as preferably lauryl alcohol, myristyl alcohol, pentadecyl alcohol, cetyl alcohol, heptadecyl alcohol, stearyl alcohol, isostearyl alcohol, palmitoleyl alcohol as well as mixtures thereof. A particular preferred co-emulsifier is cetearyl alcohol (i.e. a mixture of cetyl-and stearyl alcohol), which is e.g. commercially available as Lanette® O from Cognis.

In a particular advantageous embodiment of the invention the phosphate ester surfactant is trilaureth-4 phosphate and the co-emulsifier is cetearyl alcohol.

The term 'liquid crystal gel network' refers to a system characterized by the formation of a reticular organised structure in liquid crystal form which exhibits the properties of both (crystalline) solids and (isotropic) liquids.

The formation of the liquid crystal gel network by the phosphate ester surfactant and the co-emulsifier within the compositions according to the present inventions can be determined by measuring the viscosity in dependence of the ratio (amount phosphate ester surfactant/amount co-emulsifier) in water as illustrated in the examples. The area of maximum viscosity (+/−20%) indicates optimum gel network formation and consequently gives the optimum ratio of phosphate ester surfactant to co-emulsifier for the purpose of the present invention.

The amount of co-emulsifier is generally selected in the range of 0.1 to 20 wt.-%, preferably from 1 to 10 wt.-%, most preferably from 2 to 6 wt.-% based on the total weight of the composition. As discussed above the optimum ratio might depend on the kind of phosphate ester surfactant and the kind of co-emulsifier selected but can easily be established by a person skilled in the art.

The ratio (w/w) of co-emulsifier to phosphate ester surfactant is advantageously selected in the range of 50:1 to 1:1, preferably in the range of 10:1 to 1.5:1, more preferably in the range of 9:1 to 2:1.

If the co-emulsifier is cetearyl alcohol and the phosphate ester surfactant is trilaureth-4 phosphate the ratio (w/w) of co-emulsifier to phosphate ester surfactant is preferably selected in the range of 9:1 to 1.5:1 such as in the range of 9:1 to 2:1 and particularly in the range of about 4:1 as this leads to an increase in viscosity [mPas] reflecting optimal liquid crystal gel network formation.

In all embodiments of the present invention the topical compositions according to the present invention are preferably emulsions emulsion comprising an aqueous phase and an oily phase, most preferably the topical compositions are O/W emulsions. Preferably, the aqueous phase constitutes at least 50 wt.-% and the oily phase at least 15 wt.-% of the composition. In particular the water phase constitutes at least 60 wt.-% and the oily phase constitutes less than 40 wt.-%. In particular the water phase constitutes at least 70 wt.-% and the oily phase constitutes less than 30 wt.-% of the composition. Most preferably, the amount of the water phase is selected in the range of 70-80 wt.-% and the amount of the oily phase is selected in the range of 20-30 wt.-% based on the total weight of the composition.

It is well understood, that the water phase and the oily phase together form the emulsion, wherein, however, minor amounts (up to 5 wt.-%) of remainder ingredients such as preservatives may also be present which may be added to one of the phases or separately e.g. at end of the preparation which is well known to a person skilled in the art.

Particular suitable oil components (including the co-emulsifier) to form the oily phase of the topical compositions according to the present invention are isopropyl palmitate, caprylic/capric triglyceride, cetearyl alcohol and isopropylpalmitate as well as mixtures thereof.

The water phase advantageously consists essentially of water, a moisturizer and a thickener. Suitable thickeners encompass e.g. Xanthan Gum such as e.g. available as Keltrol CG-RD, Guar-Gum, Alginate, Poly-acrylates, Polyquaternium, Silicone-based polymers, Carbomer, Acrylates/C10-30 Alkyl Acrylates Copolymer, Hydroxyethylcellulose. Preferred thickeners are Xanthan Gum or Acrylates/C10-30 Alkyl Acrylates Copolymers or Carbomer.

According to the invention xanthan gum is preferably used in low concentrations such as e.g. in concentrations selected in the range of 0.05-1 wt.-%, preferably in the range of 0.05-0.3 wt.-%.

According to the invention Acrylates/C10-30 Alkyl Acrylates is preferably used in low concentrations such as e.g. in concentrations selected in the range of 0.05-1 wt.-%, preferably in the range of 0.05-0.3 wt.-%.

According to the invention Carbomer is preferably used in low concentrations such as e.g. in concentrations selected in the range of 0.05-1 wt.-%, preferably in the range of 0.05-0.3 wt.-%.

A particularly suitable moisturizer is glycerine, but not limited to. Other moisturizers that can applied are: e.g. Saccharide isomerate such as e.g. available as Pentavitin®, Penthylene Glycol such as e.g. available as Hydrolite®, Propylene Glycol, Butylene Glycol, Urea, among others.

According to the invention glycerine is preferably used in low concentrations such as e.g. concentrations selected in the range of 0.5-10 wt.-% such as in the range of 1-6 wt.-%.

A particular suitable preservative to be used in the topical compositions according to the invention is methylisothiazolinone.

The term "topical composition" as used herein refers in particular to cosmetic compositions that can be topically applied to mammalian keratinous tissue such as e.g. human skin or hair, particularly human skin.

The term "cosmetic composition" as used in the present application refers to cosmetic compositions as defined under the heading "Kosmetika" in Römpp Lexikon Chemie, 10th edition 1997, Georg Thieme Verlag Stuttgart, New York as well as to cosmetic preparations as disclosed in A. Domsch, "Cosmetic Preparations", Verlag für chemische Industrie (ed. H. Ziolkowsky), 4$^{th}$ edition, 1992.

Preferably, the topical preparations according to the present invention are in the form of an emulsion or micro emulsion (in particular of O/W-type), PIT-emulsion, multiple emulsion (e. g. O/W/O-type and W/O/W) or pickering emulsion.

In a particular preferred embodiment, the topical compositions according to the invention are O/W emulsions.

Topical compositions in accordance with the invention can be in the form of a liquid, lotion, a thickened lotion, a gel, a cream, a milk, an ointment or paste, and can be optionally be packaged as an aerosol and can be provided in the form of a mousse such as a aerosol mousse, a foam or a spray foam, a spray, a stick.

In accordance with the present invention, the topical compositions according to the invention may optionally be combined with further ingredients such as ingredients for skin lightening; tanning prevention; treatment of hyperpigmentation; preventing or reducing acne, wrinkles, lines, atrophy and/or inflammation; chelators and/or sequestrants; anti-cellulites and slimming (e.g. phytanic acid), firming, moisturizing and energizing, self tanning, soothing, as well as agents to improve elasticity and skin barrier and/or UV-filter substances and carriers and/or excipients or diluents conventionally used in topical compositions. If nothing else is stated, the excipients, additives, diluents, etc. mentioned in the following are suitable for topical preparations according to the present invention. The necessary amounts of the cosmetic and dermatological adjuvants and additives can, based on the desired product, easily be determined by the skilled person.

The cosmetically active ingredients useful herein can in some instances provide more than one benefit or operate via more than one mode of action.

Preferred examples of further ingredients are vitamin C (ascorbic acid) and/or its derivatives (e.g. ascorbyl phosphate such as Stay C (sodium ascorbyl monophosphate) from DSM Nutritional Products Ltd.), vitamin A and/or its derivatives (e.g., retinoid derivatives such as retinyl palmitate or retinyl propionate), vitamin E and/or its derivatives (e.g., tocopherol acetate), vitamin $B_6$, vitamin $B_{12}$, biotin, co-enzyme Q10, EGCG, hydroxytyrosol and/or olive extract, shea butter, algae extract, cocoa butter, aloe extract, jojoba oil, echinacea extract, chamomile extract, Glycyrrhetinic Acid, Glycyryca Glabra extract, in particular vitamin E and/or its derivatives, shea butter, algae extract, cocoa butter, aloe extract and or vitamin A and/or its derivatives. The additional cosmetically active ingredient is typically included in an amount of at least 0.001 wt. % based on the total weight of the topical preparation. Generally, an amount of about 0.001 wt. % to about 30 wt. %, preferably from about 0.001 wt. % to about 10 wt. % of an additional cosmetically active agent is used.

A vitamin E derivative for use in the present invention is tocopheryl acetate. Tocopheryl acetate may be present in the topical preparations in an amount from about 0.05 wt.-% to about 25 wt.-%, in particular 0.5 wt.-% to 5 wt.-%. Another vitamin E derivative of interest is tocopheryl linoleate. Tocopheryl linoleate may be present in the skin care composition in an amount from about 0.05 wt.-% to about 25 wt.-% in particular 0.05 wt.-% to 5 wt.-%.

Vitamin A and/or its derivatives in particular retinoid derivatives such as retinyl palmitate or retinyl propionate is preferably used in the topical preparations according to the invention in an amount of 0.01-5 wt.-%, in particular 0.01-0.3 wt.-%.

Suitable UV-filter substance to be incorporated into the topical compositions according to the present invention are conventional UVA and/or UVB and or broad spectrum UV-filter substances known to be added into topical compositions such as cosmetic or dermatological sun care products. Such UV-filter substances comprise all groups which absorb light in the range of wavelengths 400 nm to 320 nm (UVA) and 320 nm to 280 nm (UVB) or of even shorter wavelengths (UVC) and which are or can be used as cosmetically acceptable UV-filter substances. Such UV-filter substances are e.g. listed in the CTFA Cosmetic ingredient Handbook or "The Encyclopedia of Ultraviolet Filters" (ISBN: 978-1-932633-25-2) by Nadim A. Shaath.

Suitable UV-filter substances may be organic or inorganic compounds. Exemplary organic UV-filter substances encompass e.g. acrylates such as e.g. 2-ethylhexyl 2-cyano-3,3-diphenylacrylate (octocrylene, PARSOL® 340), ethyl 2-cyano-3,3-diphenylacrylate; Camphor derivatives such as e.g. 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, terephthalylidene dicamphor sulfonic acid (Mexoryl® SX); Cinnamate derivatives such as e.g. ethylhexyl methoxycinnamate (PARSOL® MCX), ethoxyethyl methoxycinnamate, isoamyl methoxycinnamate as well as cinnamic acid derivatives bond to siloxanes; p-Aminobenzoic acid derivatives such as e.g. p-aminobenzoic acid, 2-ethylhexyl p-dimethylaminobenzoate, N-oxypropylenated ethyl p-aminobenzoate, glyceryl p-aminobenzoate; Benzophenones such as e.g. benzophenone-3, benzophenone-4, 2,2',4,4'-tetrahydroxy-benzophenone, 2,2'-dihydroxy-4,4'-dimethoxybenzophenone; Esters of benzalmalonic acid such as e.g. di-(2-ethylhexyl) 4-methoxybenzalmalonate; Organosiloxane compounds carrying chromophore groups such as e.g. polysilicones-15 (PARSOL® SLX), drometrizole trisiloxane (Mexoryl® XL); Imidazole derivatives such as e.g. 2-phenyl benzimidazole sulfonic acid (PARSOL®HS) and salts thereof such as e.g. sodium- or potassium salts, ammonium salts, morpholine salts, salts of primary, sec. and tert. amines like monoethanolamine salts, diethanolamine salts; Salicylate derivatives such as e.g. isopropylbenzyl salicylate, benzyl salicylate, butyl salicylate, ethylhexyl salicylate (PARSOL® EHS, Neo Heliopan® OS), isooctyl salicylate or homomenthyl salicylate (homosalate, PARSOL® HMS, Neo Heliopan® HMS); Triazine derivatives such as e.g. ethylhexyl triazone (Uvinul® T-150), diethylhexyl butamido triazone (Uvasorb® HEB), bis-ethylhexyloxyphenol methoxyphenyl triazine (Tinosorb® S); Benzotriazole derivatives such as e.g. 2,2'-methylene-bis-(6-(2H-benzotriazole-2-yl)-4-(1,1,3,3,-tetramethylbutyl)-phenol (Tinosorb® M); Encapsulated UV-filters such as e.g. encapsulated ethylhexyl methoxycinnamate (Eusolex® UV-pearls) or microcapsules loaded with UV-filters as e.g. disclosed in EP 1471995; Dibenzoylmethane derivatives such as e.g. 4-tert.-butyl-4'-methoxydibenzoyl-methane (PARSOL® 1789), dimethoxydibenzoylmethane, isopropyldibenzoylmethane; Phenylene-1,4-bis-benzimidazolsulfonic acids or salts such as e.g. 2,2-(1,4-phenylene)bis-(1H-benzimidazol-4,6-disulfonic acid) (Neoheliopan AP); Amino substituted hydroxybenzophenones such as e.g. 2-(4-diethylamino-2-hydroxy-benzoyl)-benzoic acid hexylester (Aminobenzophenon, Uvinul® A Plus); Benzoxazol-derivatives such as e.g. 2,4-bis[5-1(dimethylpropyl)benzoxazol-2-yl-(4-phenyl)-imino]-6-(2-ethylhexyl)-imino-1,3,5-triazin [Uvasorb® K2A); Inorganic UV-filter substances encompass pigments such as e.g. microparticulated Zink oxide or Titanium dioxide (e.g. commercially available as PARSOL® TX) The term "microparticulated" refers to a particle size from about 5 nm to about 200 nm, particularly from about 15 nm to about 100 nm. The particles may also be coated by other metal oxides such as e.g. aluminum or zirconium oxides or by organic coatings such as e.g. polyols, methicone, aluminum stearate, alkyl silane. Such coatings are well known in the art.

In order to enhance the photostability of sun care products it may be desirable to add a photostabilizer. Exemplary photostabilizers known to a skilled person in the art encompass e.g. 3,3-diphenylacrylate derivatives such as e.g. octocrylene (PARSOL® 340) or Polyester-8 (Polycrylene®); Benzylidene camphor derivatives such as e.g. 4-methyl benzylidene camphor (PARSOL® 5000); Benzalmalonate derivatives such as e.g. polysilicones-15 (PARSOL® SLX) or diethylhexyl syringylidene malonate (Oxynex ST liquid); Dialkyl naphthalates such as diethylhexyl naphthalate (Corapan TQ) without being limited thereto. An overview on further stabilizers is e.g. given in 'SPF Boosters & Photostability of Ultraviolet Filters', HAPPI, October 2007, p. 77-83 which is included herein by reference. The photostabilizers are generally used in an amount of 0.05 to 10 wt.-% with respect to the total weigh of the topical composition.

Generally, the amount of each UV-filter substance in the topical compositions according to the invention is selected in the range of about 0.1 to 10 wt.-%, preferably in the range of about 0.2 to 7 wt.-%, most preferably in the range of about 0.5 to 5 wt.-% with respect to the total weigh of the topical composition.

The total amount of UVA-filter substance(s), in particular of butyl methoxydibenzoylmethane, in the topical compositions according to the invention is preferable selected in the range of about 2 to 8 wt.-%, in particular in the range of about 4 to 6 wt.-%, most particular in the range of about 4 to 5 wt.-% with respect to the total weight of the topical composition.

The total amount of UV-filter substances in the topical compositions according to the invention is preferably in the range of about 1 to 40 wt.-%, preferably in the range of about 5 to 30 wt.-%, in particular in the range of 20 to 30 wt.-% with respect to the total weight of the topical composition.

Preferred UVB-filter substances according to the invention encompass polysilicones-15, phenylbenzimidazol sulfonic acid, octocrylene, ethylhexyl methoxycinnamate, ethyl hexylsalicylate and/or homosalate.

Preferred broadband UV-filter substances according to the invention encompass unsymmetrical s-triazine derivatives such 2,4-Bis-{[4-(2-ethyl-hexyloxy)-2-hydroxy]-phenyl}-6-(4-methoxyphenyl)-1,3,5-triazin, certain benzophenones such as e.g. 2-Hydroxy-4-methoxy-benzophenon, 2,2'-Methylen-bis-(6-(2H-benzotriazol-2-yl)-4-(1,1,3,3-tetramethyl-butyl)-phenol), and or titanium dioxide.

The preferred UVA-filter substance according to the invention is butyl methoxydibenzoylmethane. Preferably, butyl methoxydibenzoylmethane is the only UVA-filter substance in the topical compositions according to the invention.

The topical cosmetic compositions of the invention can also contain usual cosmetic adjuvants and additives, such as preservatives antioxidants, fatty substances/oils, water, organic solvents, silicones, thickeners, softeners, emulsifiers, sunscreens, antifoaming agents, moisturizers, aesthetic components such as fragrances, surfactants, fillers, sequestering agents, anionic, cationic, nonionic or amphoteric polymers or mixtures thereof, propellants, acidifying or basifying agents, dyes, colorings/colorants, abrasives, absorbents, essential oils, skin sensates, astringents, antifoaming agents, pigments or nanopigments, e.g. those suited for providing a photoprotective effect by physically blocking out ultraviolet radiation, or any other ingredients usually formulated into cosmetic compositions. Such cosmetic ingredients commonly used in the skin care industry, which are suitable for use in the compositions of the present invention are e.g. described in the CTFA Cosmetic Ingredient Handbook, Second Edition (1992) without being limited thereto.

The necessary amounts of the cosmetic and dermatological adjuvants and additives can —based on the desired product— easily be chosen by a skilled person in this field and will be illustrated in the examples, without being limited hereto.

Of course, one skilled in this art will take care to select the above mentioned optional additional compound or compounds and/or their amounts such that the advantageous properties intrinsically associated with the combination in accordance with the invention are not, or not substantially, detrimentally affected by the envisaged addition or additions.

The topical compositions according to the present invention preferably have a viscosity of at least 1000 mPs (determined by TA Instruments AR 550, Shear rate 1 s$^{-1}$, 25° C., plate SST ST 40 mm), preferably in the range of 2000-15000 mPas such as in the range of 5000-13000 mPas.

The topical compositions according to the invention have a pH in the range of 3-10, preferably in the range of pH of 4-8, most preferred in the range of pH 4-7.

The following examples are provided to further illustrate the compositions and effects of the present invention. These examples are illustrative only and are not intended to limit the scope of the invention in any way.

EXAMPLE 1

Solubility of Resveratrol in Phosphate Ester

To evaluate solubility of resveratrol in trilaureth-4 phosphate, the following procedure was adopted: lab glass beakers of 250 ml capacity were filled with the phosphate ester surfactant in the range as indicated in Table 1. They were heated up to 40° C. and immediately after, resveratrol was added in the same ratio as provided in Table 1. The final volume was 50 ml. Solubilization occurs almost instantaneously, however the beakers were vigorously shaken for about 1 minute at 6000 rpm. Level of solubility was judged by visual observation of transparency.

TABLE 1

Solubility of Resveratrol in Trilaureth-4 Phosphate

| | Concentration wt.-% | | | | | |
|---|---|---|---|---|---|---|
| Resveratrol | 2 | 4 | 6 | 8 | 10 | 12 |
| Trilaureth-4-phosphate | 98 | 96 | 94 | 92 | 90 | 88 |
| Solubility | +++ | +++ | +++ | +++ | +++ | ++ |

(from + = partially to +++ = fully soluble)

As it can be retrieved from table 1, resveratrol is highly compatible with the phosphate ester surfactant trilaureth-4 phosphate. Resveratrol solubilizes well in this emulsifier already at room temperature. Its solubility was almost instantaneous when heated up to 40° C. The threshold level of its solubility in this kind of emulsifier was determined to be around 10% (Table 1).

EXAMPLE 2

Development and Optimization of Liquid Crystal Gel Network

The following operating conditions were applied:
Emulsification mixture→10% wt
Ratio range, Phosphate-Ester/Cetearyl Alcohol→0.5/9.5 to 6/4

While the performance index was defined as the viscosity of the gel structure, the optimization criterion was to find the optimum ratio that delivered highest viscosity. This has been monitored using rheological and microscopic techniques.

The following procedure was adopted to produce liquid crystal gel network structure. In a first step, Phase A (water 90% wt) and Phase B (emulsifier/co-emulsifier mixture 10% wt) were prepared and heated up to approximately 75° C. The exact ratios cascade is given in Table 2. Phase B was added to Phase A and was then vigorously shaken for about 1 minute at 6000 rpm. After this procedure an emulsion is produced. By cooling slowly this emulsion, a liquid crystal gel network is formed at room temperature. After 24 h at room temperature, the viscosity was determined. The viscosity profile depicted by each ratio can be observed in Table 2. From these results, the ratio of phosphate ester to cetearyl alcohol that developed the maximum viscosity was determined to be 2 to 8 (1 to 4).

TABLE 2

Experimental set-up to find the most appropriate ratio of phosphate ester surfactant to co-emulsifier.

| | I | II | III | IV | V | VI | VII |
|---|---|---|---|---|---|---|---|
| | | | | Wt.-% | | | |
| Phase A | | | | | | | |
| Water | 90 | 90 | 90 | 90 | 90 | 90 | 90 |
| Phase B | | | | | | | |
| Phosphate ester surfactant: Trilaureth-4-phosphate | 0.5 | 1 | 2 | 3 | 4 | 5 | 6 |
| Lipophilic co-emulsifier: Cetearyl alcohol | 9.5 | 9 | 8 | 7 | 6 | 5 | 4 |
| Total | 100 | 100 | 100 | 100 | 100 | 100 | 100 |
| Viscosity [mPas] | 5190 | 8517 | 9416 | 7790 | 6674 | 3633 | 1785 |

EXAMPLE 3 a.) Formulation of resveratrol in an emulsion having a liquid crystal gel network and having consistency of a lotion

| Phase | Ingredients | INCI Name | % w/w |
|---|---|---|---|
| A | Water demineralized. | Aqua | 75.65 |
| | Glycerin | Glycerin | 3.00 |
| | Keltrol CG-RD | Xanthan Gum | 0.15 |
| B | Phosphate Ester | Trilaureth-4 Phosphate | 1.00 |
| | Resveratrol | Resveratrol | 0.10 |
| C | Cetearyl Alcohol | Cetearyl Alcohol | 4.00 |
| | IPP | Isopropyl Palmitate | 8.00 |
| | Myritol 318 | Caprilic/Capric Triglyceride | 8.00 |
| D | Neolone 950 | Methylisothiazolinone | 0.10 |

1$^{st}$ Mix all the ingredients of the water Phase A and heat up to 40° C.

2$^{nd}$ Dissolve resveratrol in the phosphate ester surfactant, mix them and heat up to 40° C. The solution must be completely clear (Phase B).

3$^{rd}$ Mix all the ingredients of the Phase C and heat up to 75° C.

3$^{rd}$ Add Phase B into the oily phase C and mix gently. Immediately after, add this mixture into the aqueous phase A. Homogenize thoroughly (13000 min$^{-1}$)

4$^{th}$ At last, add Phase D under continuous and gentle mixing. Stir gently for 1 h, after which homogenize once more for 1 min at lower speed (9000 min$^{-1}$)

Viscosity: 6000 mPas

The liquid crystal gel network developed in this example was able to carrier resveratrol in a stable manner. No precipitation of resveratrol was observed even after 1344 days after preparation.

b.) Formulation of resveratrol in an emulsion having a liquid crystal gel network and having consistency of a cream

| Phase | Ingredients | INCI Name | % w/w |
|---|---|---|---|
| A | Water demineralized | Aqua | 70.65 |
|  | Glycerin | Glycerin | 3.00 |
|  | Keltrol CG-RD | Xanthan Gum | 0.15 |
| B | Phosphate Ester | Trilaureth-4 Phosphate | 2.00 |
|  | Resveratrol | Resveratrol | 0.20 |
| C | Ceteraryl Alcohol | Ceteraryl Alcohol | 8.00 |
|  | IPP | Isopropyl Palmitate | 8.00 |
|  | Myritol 318 | Caprilic/Capric Triglyceride | 8.00 |
| D | Neolone 950 | Methylisothiazolinone | 0.10 |

Preparation Procedure $1^{st}$ Mix all the ingredients of the water phase A and heat up to 40° C.

$2^{nd}$ Dissolve resveratrol in the phosphate ester surfactant, mix them and heat up to 40° C. The solution must be completely clear (Phase B).

$3^{rd}$ Mix all the ingredients of the phase C and heat up to 75° C.

$3^{rd}$ Add Phase B into the oily phase C and mix gently. Immediately after, add this mixture into the aqueous phase A. Homogenize thoroughly (13000 $min^{-1}$)

$4^{th}$ At last, add Phase D under continuous and gentle mixing. Stir gently for 1 h, after which homogenize once more for 1 min at lower speed (9000 $min^{-1}$)

Viscosity: 12060 mPas

The liquid crystal gel network showed the same stability as seen with the lotion formulation. No precipitations of resveratrol could be observed after long storage period.

Furthermore, the lotion as well as the cream exhibited an excellent skin feeling. Both, the lotion and the cream showed good dispersion on the skin and left fresh, light, and pleasant sensation on the skin.

The invention claimed is:

1. A topical composition comprising resveratrol, wherein the resveratrol is incorporated into a liquid crystal gel network formed by trilaureth-4 phosphate and a solid co-emulsifier.

2. The topical composition according to claim 1, wherein the topical composition is an emulsion comprising an aqueous phase and an oily phase.

3. The topical composition according to claim 2, wherein the topical composition is an O/W emulsion.

4. The topical composition according to claim 1, wherein the trilaureth-4 phosphate is present in an amount within a range of 0.1 to 5 wt. % based on total weight of the composition.

5. The topical composition according to claim 1, wherein the co-emulsifier has a HLB value <5.

6. The topical composition according to claim 1, wherein the co-emulsifier comprises at least one non-ionic solid fatty alcohol having from 12 to 22 carbon atoms.

7. The topical composition according to claim 1, wherein the co-emulsifier is present in an amount within a range of 0.1 to 20 wt. % based on total weight of the composition.

8. The topical composition according to claim 1, wherein the resveratrol is present in an amount within a range of 0.01 to 2 wt. % based on total weight of the composition.

9. The topical composition according to claim 1, wherein the co-emulsifier and the trilaureth-4 phosphate are present in a weight ratio (w/w) of co-emulsifier to trilaureth-4 phosphate of 50:1 to 1:1.

10. The topical composition according to claim 1, wherein the trilaureth-4 phosphate and the resveratrol are present in a weight ratio (w/w) of trilaureth-4 phosphate to resveratrol of 200:1 to 5:1.

11. The topical composition according to claim 2, wherein the aqueous phase constitutes at least 50 wt. % based on total weight of the composition and the oily phase constitutes at least 15 wt. % based on total weight of the composition.

12. The topical composition according to claim 6, wherein the co-emulsifier comprises cetearyl alcohol.

13. A process for the preparation of a topical composition according to claim 1 which comprises an aqueous phase and an oily phase, wherein the process comprising the steps of:
  (a) dissolving resveratrol in trilaureth-4 phosphate by applying heat followed by either,
  (b1) adding the resveratrol/trilaureth-4 phosphate solution to the heated oily phase comprising the solid co-emulsifier followed by addition of the heated aqueous phase, or
  (b2) adding the resveratrol/trilaureth-4 phosphate solution to the heated aqueous phase followed by the addition of the resulting mixture to the heated oily phase comprising the solid co-emulsifier, followed by
  (c) homogenizing the resulting mixture to obtain the liquid crystal gel network.

14. The process according to claim 13, wherein the trilaureth-4 phosphate is present in an amount to provide a weight ratio (w/w) of trilaureth-4 phosphate to resveratrol of 200:1 to 9:1.

15. The process according to claim 14, wherein the co-emulsifier is cetearyl alcohol which is present to provide a weight ratio (w/w) of cetearyl alcohol to trilaureth-4 phosphate of 50:1 to 1:1.

* * * * *